(12) United States Patent
Liu

(10) Patent No.: US 11,351,184 B2
(45) Date of Patent: Jun. 7, 2022

(54) **PREPARATION OF *PULSATILLA SAPONIN* B4 FOR INJECTION**

(71) Applicant: Qi Liu, Beijing (CN)

(72) Inventor: Qi Liu, Beijing (CN)

( * ) Notice: Subject to any disclaimer, the term of this patent is extended or adjusted under 35 U.S.C. 154(b) by 50 days.

(21) Appl. No.: 16/629,002

(22) PCT Filed: Jul. 7, 2017

(86) PCT No.: PCT/CN2017/092199
§ 371 (c)(1),
(2) Date: Jan. 6, 2020

(87) PCT Pub. No.: WO2019/006741
PCT Pub. Date: Jan. 10, 2019

(65) Prior Publication Data
US 2020/0197425 A1    Jun. 25, 2020

(51) Int. Cl.
*A61K 31/704* (2006.01)
*A61K 9/19* (2006.01)
*A61K 9/08* (2006.01)
*A61K 9/00* (2006.01)

(52) U.S. Cl.
CPC .............. *A61K 31/704* (2013.01); *A61K 9/08* (2013.01); *A61K 9/19* (2013.01); *A61K 9/0019* (2013.01)

(58) Field of Classification Search
None
See application file for complete search history.

(56) References Cited

FOREIGN PATENT DOCUMENTS

| CN | 1895314 | * | 1/2007 | ........... A61K 31/704 |
|---|---|---|---|---|
| CN | 102068509 | * | 5/2011 | ............. G01N 21/33 |
| CN | 102234305 | * | 11/2011 | ............. C07J 63/00 |
| CN | 102234305 | A | 11/2011 | |
| CN | 105213410 | A | 1/2016 | |
| CN | 106389408 | A | 2/2017 | |
| JP | 3-93725 | A | 4/1991 | |
| JP | 2002-528511 | A | 9/2002 | |
| JP | 2008-508263 | A | 3/2008 | |

OTHER PUBLICATIONS

English machine translation of CN102068509 above, downloaded from translationportal.epo.org (Year: 2011).*
English abstract and machine translation of CN 102068509 above, downloaded from worldwide.espacenet.com (Year: 2011).*
English abstract and machine translation of CN 102234305 above, downloaded from worldwide.espacenet.com (Year: 2011).*
Ye et al., "New Lupane Glycosides from Pulsatilla Chinensis" Planta Medica vol. 68 pp. 183-186 (Year: 2002).*
English machine translation of CN1895314, downloaded from https://translationportal.epo.org/ (Year: 2007).*

* cited by examiner

*Primary Examiner* — Eric Olson
(74) *Attorney, Agent, or Firm* — Lewis Roca Rothgerber Christie LLP

(57) ABSTRACT

Disclosed is a preparation of *Pulsatilla* saponin B4 for injection, comprising *Pulsatilla* saponin B4 and a pharmaceutically acceptable excipient. The preparation is an aqueous injection or a lyophilized powder injection, more preferably a lyophilized powder injection. Methods for preparing the *Pulsatilla* saponin B4 aqueous injection and the *Pulsatilla* saponin B4 lyophilized powder injection comprise dissolution, fluid preparation, filtration and other steps. The preparation of *Pulsatilla* saponin B4 for injection has a low effective dose for reversing renal injury caused by cisplatin, significantly improves the medication safety of *Pulsatilla* saponin B4, and is expected to provide a new option for the clinical treatment of renal injuries and renal failure.

9 Claims, No Drawings

PREPARATION OF *PULSATILLA SAPONIN* B4 FOR INJECTION

CROSS-REFERENCE TO RELATED APPLICATION(S)

This application is a U.S. National Phase Patent Application and claims priority to International Application Number PCT/CN2017/092199, filed on Jul. 7, 2017, the entire contents of which are incorporated herein by reference.

TECHNICAL FIELD

The present invention belongs to the field of pharmaceutical preparation, particularly relates to a preparation for injection with *Pulsatilla* saponin B4 as the active ingredient.

BACKGROUND ART

Chinese herb medicine RadixPulsatiliae Chinese is a dry root of *Pulsatilla chinensis* (Bge.) Regel of family Ranunculaceae, it was first recorded in *Shennong's Classic of Materia Medica*, and is a commonly used Traditional Chinese medicine. It owns the property of bitter and cold, and has the functions of clearing heat and detoxifying, cooling blood and checking dysentery, and drying dampness and killing insects, and is used to treat dysentery with blood stool due to heat-toxicity, warm malaria with chill and fever, epistaxis and hemorrhoids with blood stool. Modern pharmacological studies have demonstrated that Radix Pulsatiliae Chinese has a wide range of antibacterial activities, and has inhibitory effects on *Staphylococcus aureus, Bacillus dysteriae*, dermatophytes, yeast, *Candida albicans* and so on. The antitumor effect of Radix Pulsatiliae Chinese is also a research hotspot. In addition, Radix Pulsatiliae Chinese has the functions of anti-inflammatory and immune enhancement.

Radix Pulsatiliae Chinese is rich in triterpenoid saponins. *Pulsatilla* saponin B4 belongs to a lupine-type pentacyclic triterpenoid saponin having the structure of Formula 1.

*Pulsatilla* saponin B4 has strong activity. For example, Chinese patent publication No. CN105213410A (publication date: Jan. 6, 2016) discloses a use of *Pulsatilla* saponin B4 as an immunomodulator in the treatment of acute inflammation which includes acute renal injury, acute liver injury and acute lung injury caused by overexpression of inflammatory factors. For another example, Chinese patent publication No. CN105535004A (publication date: May 4, 2016) discloses a use of the compound as an EV71 virus inhibitor in the preparation of anti hand-foot-and-mouth disease drugs.

*Pulsatilla* saponin B4 has five glycosyl groups and has good water solubility. Research has demonstrated that if the compound is administered orally (such as by gavage in animal experiments), the effective dose is large, resulting in a narrow safety window. Therefore, it is necessary to develop a non-oral preparation of *Pulsatilla* saponin B4 in order to facilitate the active role in a safe dose range to meet the clinical medical needs. However, till now, there has been no report on the *Pulsatilla* saponin B4 injection.

SUMMARY OF THE INVENTION

In order to overcome the disadvantages of the prior art, the present invention provides a *Pulsatilla* saponin B4 preparation for injection. The preparation is stable and easy to prepare. Compared with oral administration, the effective dose of the preparation of *Pulsatilla* saponin B4 for injection to reverse cisplatin-induced renal injury is reduced by 20 times, thereby improving drug safety, therefore, this preparation is promising to provide a new choice for clinical treatment of renal injury and renal failure.

In order to achieve the aforesaid aim, the present invention provides the following technical solution:

A *Pulsatilla* saponin B4 preparation for injection, comprising *Pulsatilla* saponin B4 and a pharmaceutically acceptable excipient, wherein the preparation is an aqueous injection or a lyophilized powder for injection.

Preferably, the *Pulsatilla* saponin B4 preparation for injection consists of *Pulsatilla* saponin B4, a pharmaceutically acceptable excipient and unavoidable impurities.

Preferably, the *Pulsatilla* saponin B4 preparation for injection is an intramuscular injection and/or an intravenous injection; more preferably an intravenous injection.

Formula 1

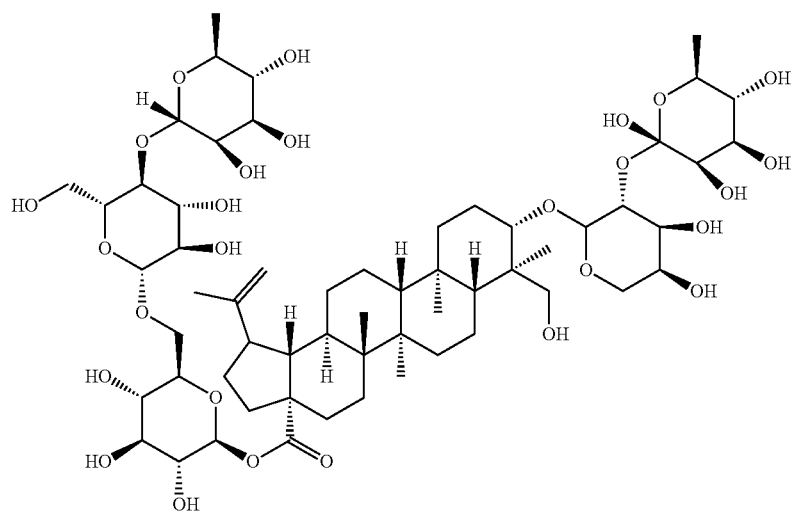

Preferably, the *Pulsatilla* saponin B4 preparation for injection is an aqueous injection, wherein the pharmaceutically acceptable excipient is water for injection.

Preferably, the mass percentage of the *Pulsatilla* saponin B4 in the aqueous injection is 0.5%~5%, more preferably 2~3%.

The present invention also provides a method for preparing the aqueous injection, comprising dissolving, decolorizing by active carbon, filtrating, making up to the final volume, sub-packing and sterilizing.

Preferably, the specific method for preparing the aqueous injection is as follows:

Taking a prescribed amount of *Pulsatilla* saponin B4, weighing precisely, adding part of water for injection, stirring to dissolve *Pulsatilla* saponin B4 completely, then adding 0.1%~0.5% of active carbon based on the total mass of the aqueous injection to the solution, heating to boil, stirring for 15 minutes, making up to the final volume with water for injection, mixing well, filtering while hot with a 0.22 μm microporous filter membrane to remove the active carbon, thereby obtaining an intermediate solution; sub-packing and sterilizing to obtain the aqueous injection.

In the method for preparing the aqueous injection, the sub-packing and sterilizing operation are carried out according to the conventional method in the art. For example, the sterilizing operation may be sterilization by hot pressing, sterilization at 115° C. for 30 min or sterilization at 121° C. for 15 min.

More preferably, the *Pulsatilla* saponin B4 preparation for injection according to the present invention is a lyophilized powder for injection, the pharmaceutically acceptable excipient is a lyophilized excipient, which is one or more (may be in any ratio) selected from the group consisting of lactose, sucrose and mannitol.

Preferably, the mass ratio of the *Pulsatilla* Saponin B4 to the lyophilized excipient in the lyophilized powder for injection is 3:10~3:16.

More preferably, the mass ratio of *Pulsatilla* saponin B4 to the lyophilized excipient in the lyophilized powder for injection is 3:14.

Further preferably, the lyophilized excipient is mannitol.

The present invention also provides a method for preparing the lyophilized powder for injection comprising the steps of the preparation and freeze-drying of the intermediate solution.

Preferably, the specific preparation of the intermediate solution is as follows:

Dissolving the *Pulsatilla* saponin B4 into water for injection, stirring to dissolve, adding the lyophilized excipient according to the mass ratio, stirring, adjusting the pH to 6.0~8.5, adding 0.05%~0.1% of the active carbon based on the total mass of the intermediate solution, heating at 100° C. and stirring for 10~20 min, cooling to room temperature, adding water for injection till the concentration of the *Pulsatilla* saponin B4 is 0.5%~5%, filtering with a 0.22 μm microporous filter membrane to obtain the intermediate solution;

More preferably, the specific preparation of the intermediate solution is as follows:

Dissolving the *Pulsatilla* saponin B4 into water for injection, stirring to dissolve, adding the lyophilized excipient according to the mass ratio, stirring, adjusting the pH to 6.5~8.0, adding 0.05% of active carbon based on the total mass of the intermediate solution, heating at 100° C. and stirring for 10~20 min, cooling to room temperature, adding water for injection till the concentration of the *Pulsatilla* saponin B4 is 2%~3%, filtering with a 0.22 m microporous filter membrane to obtain the intermediate solution.

Preferably, the freeze-drying of the intermediate solution comprises pre-freezing, sublimating and desorption drying; the temperature for pre-freezing is −30° C.~−15° C.; the vacuum pressure during the sublimating and desorption drying stage is 0.5~10 Pa; the temperature for sublimating is −10° C.~0° C.; and the temperature for desorption drying is 25° C.~30° C.;

More preferably, the vacuum pressure during the sublimating and desorption drying stage is 5~10 Pa.

More preferably, the temperature for sublimating is −10° C.

As a preferred embodiment, the specific freeze-drying operation is as follows:

Sub-packing the intermediate solution, transferring into a freezing equipment, reducing the temperature to −30° C.~−15° C. at a rate of 3.0° C.~5.0° C./min or 1.0° C.~1.5° C./min, and freezing at this temperature for 8~10 hours; then placing in a closed equipment, raising evenly the temperature to −10° C.~0° C. at a rate of 25° C.~30° C./3 h under a vacuum pressure of 0.5~10 Pa, keeping at this temperature for 8~10 h, raising the temperature to 25° C.~30° C. at a rate of 1.0° C.~1.5° C./min under the same vacuum pressure, and keeping at this temperature for 4~6 hours;

As a more preferred embodiment, the specific freeze-drying operation is as follows:

Sub-packing the intermediate solution, transferring into a freezing equipment, reducing the temperature to −30° C.~−20° C. at a rate of 3.0° C.~5.0° C./min or 1.0° C.~1.5° C./min, and freezing at this temperature for 8 hours; then placing in a closed container, raising evenly the temperature to −10° C. at a rate of 25° C.~30° C./3 h under a vacuum pressure of 5~10 Pa, keeping at this temperature for 8 h, raising the temperature to 25° C. at a rate of 1.0° C.~1.5° C./min under the same vacuum pressure, and keeping at this temperature for 4 h.

The present invention also provides a lyophilized powder of *Pulsatilla* saponin B4 for injection obtained by the preparation method.

In addition, the present invention also provides a use of the *Pulsatilla* saponin B4 preparation for injection, the aqueous injection of *Pulsatilla* saponin B4 or the lyophilized powder of *Pulsatilla* saponin B4 for injection obtained by the preparation method in the preparation of drugs for acute renal injury, chronic renal failure and/or renal insufficiency.

The "unavoidable impurities" in the description of the present invention include substances produced by the degradation of a small amount of *Pulsatilla* saponin B4, and a small amount of water in the lyophilized powder of *Pulsatilla* saponin B4 for injection. Although the unavoidable impurities exist, the content should meet the limit provision in the pharmacopoeia.

The *Pulsatilla* saponin B4 preparation for injection according to the present invention is administered to mammals, in particular to human beings. When the preparation is administered to a human being, the daily dose is 2-120 mg for an adult with a body weight of 60 kg.

The aqueous injection of *Pulsatilla* saponin B4 or the lyophilized powder of *Pulsatilla* saponin B4 for injection achieves the intramuscular injection or intravenous injection of *Pulsatilla* saponin B4 and ensures that the active ingredient enters the circulatory system in its original form and distributes to various organs in the body, especially kidney and lung etc, which enables *Pulsatilla* saponin B4 to work effectively at a much lower dose, thereby expanding the safety window for treatment and finally ensuring the safety of medication.

*Pulsatilla* saponin B4 has good water solubility and is easy to be prepared into an aqueous injection; but its stability changes with different solvents, therefore, the solvent of the aqueous injection needs to be carefully studied and selected.

*Pulsatilla* saponin B4 itself and its aqueous solution are sensitive to temperature and light; for example, after the aqueous solution of *Pulsatilla* saponin B4 was placed for 14 days at 60° C., the purity of *Pulsatilla* saponin B4 decreased from 98.90% at day 0 to 93%, the total impurities increased from 0.64% at day 0 to 0.94%. The lyophilized powder of *Pulsatilla* saponin B4 for injection is preferred because the low water content is more beneficial to the stability of the preparation.

However, in view of the complexity of lyophilized dispersion system, it is not easy to obtain the powder for injection efficiently and quickly that meets the injection requirements. Up to now, a mature theory for the selection of lyophilized formulation has not been formed yet, and individual or joint investigations of various factors that may affect the lyophilized behavior and lyophilized effect are required. Excipients and other additives in the lyophilized formulation will interact with active ingredients, and the composition and concentration of the formulation will significantly affect the freeze-solidification and sublimation dehydration behavior of the system, such as glass transition temperature at the maximum freezing concentration (an important indicator for measuring whether the collapse occurs during drying), the minimum freezing temperature, the cooling rate and the freezing annealing time etc. In addition, the type and concentration of additives will significantly affect the time consumed during drying stage and the properties of the final product. In the present invention, the parameters such as the type and amount of lyophilized excipients, the pH of the intermediate solution, the pre-freezing temperature, the pre-freezing method, the sublimation temperature, the vacuum pressure, and the desorption drying temperature are investigated separately or in combination to obtain the most preferred parameters, thereby a *Pulsatilla* saponin B4 lyophilized powder for injection with desirable appearance, good re-solubility and stable quality is obtained.

DETAILED DESCRIPTION OF THE INVENTION

The present invention is further explained with reference to the specific examples below. Those skilled in the art will understand that these examples are only used to illustrate the present invention, but not to limit the scope of the present invention in any way.

Unless otherwise specified, the experimental methods in the following examples are conventional methods. Unless otherwise specified, the medicinal materials and reagent materials etc in the following examples are commercially available. The sources of some reagents and raw materials are shown as follows:

*Pulsatilla* saponin B4: self-made, with a purity of no less than 98% by HPLC;

Mannitol (injection grade): F949A, Guangxi Nanning Chemistry & Pharmaceutical Co., Ltd.;

Glucose (injection grade): P20160118, Beijing Fengli Jingqiu Pharmaceutical Co., Ltd.;

Sucrose (injection grade): Lot No. 20150701, J. T Baker;

Water for injection: self-made;

Magnetic stirrer: IKA Model: R015PS25;

Freeze dryer: GZLY-1.0, Beijing Songyuan Huaxing Technology Development Co., Ltd.

The content of *Pulsatilla* saponin B4 in the following experimental examples and examples is determined according to the following method:

Chromatographic Conditions

Chromatographic column: $C_{18}$, 250 mm×4.6 mm, 5 μm

Mobile phase: acetonitrile-water (26:74) (volume ratio)

Flow rate: 1.0 ml/min

Wave length: 201 nm

Preparation of Control Solution

An appropriate amount of *Pulsatilla* saponin B4 control sample was taken, weighed precisely, placed into a 10 ml volumetric flask, added with methanol to dissolve and dilute to the mark, the solution was shaken well and filtered to obtain a solution with 1 mg *Pulsatilla* saponin B4 control sample/1 ml solution.

Preparation of Test Solution

About 25 mg of test sample was taken, weighed precisely, placed into a 25 ml volumetric flask, added with the mobile phase to dissolve and dilute to the mark, the solution was shaken well and filtered through a 0.22 μm microporous membrane, the filtrate was taken to obtain the test sample.

Determine Method

10 μl of the test solution was taken and injected into a liquid chromatograph, the chromatogram was recorded. The calculation formula was as follows:

$$\text{Content of Pulsatilla saponin } B4(\%) = \frac{A_{test\ sample} \times C_{control\ sample} \times S_{control\ sample} \times \text{Dilution Times}}{A_{control\ sample}} \times 100\%$$

wherein:

$C_{control\ sample}$—Concentration of the control sample (mg/ml);

$S_{control\ sample}$—Purity of the control sample;

$A_{control\ sample}$—Main peak area of the control solution;

$A_{test\ sample}$—Main peak area of the test solution.

Experimental Example 1 Efficacy of *Pulsatilla* Saponin B4 in Different Administration Routes

*Pulsatilla* saponin B4 was orally and intravenously administrated in parallel, the effect of *Pulsatilla* saponin B4 in different administration routes on acute nephritis in cisplatin (CDDP)-stimulated mouse serum was investigated.

1. Experiment Materials 1.1 Animals: ICR mouse, 16-18 g, male, Hunan SJA Laboratory Animal Co., Ltd., Permit No.: SCXK(Xiang) 2016-0002.

1.2 Reagents: cisplatin, 5 mg/kg of stock solution, which was prepared into a 1.5 mg/ml solution by adding an appropriate amount of physiological saline into cisplatin before use for later use.

1.3 Drugs: *Pulsatilla* saponin B4 (self-made, hereinafter referred to as "B4"), Batch No.: 20161107; Dexamethasone, 0.75 g/tablet, Anhui Golden Sun Biochemical Pharmaceutical Co., Ltd., Batch No.: 15032521.

The drugs were all prepared into a solution with a specified concentration under "Test Method" with double distilled water and administered in the prescribed manner.

1.4 Instruments: Desktop low speed centrifuge; Automatic biochemical analyzer

2. Test Method 2.1 Preparation before modeling: All animals were numbered and weighed.

2.2 Modeling method: models were made at a dose of 15 ml/kg of cisplatin, the mice in normal group were injected with physiological saline intraperitoneally and the mice in other groups were injected with cisplatin intraperitoneally.

2.3 Grouping and administration: Animals were randomly divided into seven groups, 10-12 animals in each group:

① Normal group, double distilled water was administered by gavage at a dose of 20 ml/kg·body weight;

② Model group, an equal volume of physiological saline was injected into the tail vein;

③ Dexamethasone positive group (0.5 mg/kg·body weight), dexamethasone solution was administered by gavage at a dose of 20 ml/kg·body weight;

④ B4 high-dose group administered intravenously (5 mg/kg·body weight), B4 solution was injected into the tail vein at a dose of 5 ml/kg·body weight;

⑤ B4 low-dose group administered intravenously (2.5 mg/kg·body weight), B4 solution was injected into the tail vein at a dose of 5 ml/kg·body weight;

⑥ B4 high-dose group administered by gavage (100 mg/kg·body weight), B4 solution was given by gavage at a dose of 20 ml/kg·body weight;

⑦ B4 low-dose group administered by gavage (50 mg/kg·body weight), B4 solution was given by gavage at a dose of 20 m/kg·body weight;

Drugs were administered continuously for 4 days from the day of modeling.

2.4 Indicators Detection

Urine was collected 0.5 hours after the last administration and urine protein was measured; blood was collected from the eyeball 1 hour after the administration, and the whole blood of the mice was placed at room temperature for 2 hours, centrifuged at 3500 rpm/min for 15 minutes, 200 μl supernatant was measured by an automatic biochemical analyzer to determine the total protein (TP), urea nitrogen (BUN) and creatinine (Cre).

3. Test Results

The detecting results of various indicators in each group were shown in table 1.

TABLE 1

Effects of B4 on Cisplatin-induced Acute Kidney Injury In Mice (SD ± Mean)

| Groups | Dose mg/kg | TP (g/L) | BUN (mg/dl) | Crea (umol/L) | Urine protein mg/ml |
|---|---|---|---|---|---|
| Normal | / | 49.61 ± 2.31 | 25.14 ± 4.34 | 25.56 ± 4.00 | 0.99 ± 0.11 |
| Model | / | 48.26 ± 3.19 | 61.95 ± 31.03# | 29.69 ± 3.66# | 1.26 ± 0.27# |
| Positive control | 0.5 | 52.90 ± 2.50 | 42.97 ± 27.45* | 30.10 ± 3.93 | 1.00 ± 0.27* |
| iv B4-5 | 5 | 46.58 ± 2.25 | 28.40 ± 14.30* | 24.10 ± 3.75* | 1.18 ± 0.20 |
| B4-2.5 | 2.5 | 47.58 ± 2.50 | 69.26 ± 45.76 | 29.27 ± 5.66 | 1.35 ± 0.39 |
| po B4-100 | 100 | 48.15 ± 3.68 | 40.27 ± 18.87* | 28.17 ± 3.01 | 1.19 ± 0.25 |
| B4-50 | 50 | 47.69 ± 3.17 | 50.1 ± 5.38 | 30.28 ± 4.77 | 1.37 ± 0.31 | compared with the normal group, P < 0.05;
*compared with the model group, P < 0.05.

The data from Table 1 indicated that:

① Compared with the normal group, the urine protein, urea nitrogen (BUN) and creatinine (Cre) levels in serum in the model group increased significantly (P<0.05), this indicates that the model is successfully established.

② Compared with the model group, the urea nitrogen (BUN) and urine protein levels in the positive control group decreased significantly (P<0.05).

③ Compared with the model group, when B4 was administrated intravenously at 5 mg/kg·body weight, the urea nitrogen (BUN) and creatinine (Cre) levels significantly decreased (P<0.05). Although there is no significant difference, the urine protein level shows a downward trend.

④ Compared with the model group, when B4 was administered by gavage at 100 mg/kg·body weight, only the urea nitrogen (BUN) level decreased significantly (P<0.05) in mice.

4. Conclusion

*Pulsatilla* saponin B4 has anti-cisplatin-induced renal damage, this indicates that it has prospects to be developed as a drug for treating acute and chronic nephritis and renal failure in clinical. And the administration route of *Pulsatilla* saponin B4 has an important effect on its efficacy, wherein the effects of B4 administered intravenously with 5 mg/kg·body weight is stronger than that administered by gavage with 100 mg/kg·body weight to reverse the indexes of abnormal renal function caused by cisplatin, while the dose decreases at least 20 times. Therefore, injection administration, especially intravenous injection, is of great significance for improving the efficacy and safety of *Pulsatilla* saponin B4.

Example 1 an Aqueous Injection of *Pulsatilla* Saponin B4

Prescription of 100 ml aqueous injection in the Example was as follows:

| | |
|---|---|
| *Pulsatilla* saponin B4 as raw material | 2.5 g |
| Water for injection | Added to 100 ml |
| Prepared into | 100 ml |

The injection was prepared by the method as below:

A prescription amount of *Pulsatilla* saponin B4 was taken and weighed precisely, (an appropriate amount of) part of water for injection was added, the *Pulsatilla* saponin B4 raw material was completely dissolved under magnetic stirring, 0.10% of active carbon based on the total mass of the solution was added into the solution, then heated and stirred in 100° C. water bath for 15 min, diluted with water for injection to 100 ml, shaken well, filtered with a 0.22 μm microporous filter membrane to remove the active carbon, 2 ml intermediate solution was measured precisely and filled into a 5 ml ampoule, and sterilized at 115° C. for 30 min, then the aqueous injection was obtained.

Experimental Example 2 Study on the Process of
Lyophilized Powder of *Pulsatilla* Saponin B4

1.1 Compatibility Test of Raw Materials and Excipients

*Pulsatilla* saponin B4 raw material was mixed with various excipients (water for injection, physiological saline, mannitol, lactose, sucrose and glucose) in a ratio of 1:5 (mass), and then placed under the conditions of high temperature (60° C. and 40° C.) and illumination (4500Lux±500), the samples were taken on day 0, 7 and 14 to investigate the purity of *Pulsatilla* saponin B4 and related substances. The results were shown in Table 2, Table 3 and Table 4.

TABLE 2

Compatibility Test Results of Raw Materials and Excipients on day 0

| Raw Materials and Excipients | Purity (%) | Related substances (%) | |
|---|---|---|---|
| | | Max single impurity | Total impurities |
| API* | 99.10 | 0.40 | 0.65 |
| API+ water for injection | 98.90 | 0.41 | 0.64 |
| API+ physiological saline | 99.08 | 0.41 | 0.64 |
| API+ mannitol | 99.03 | 0.40 | 0.63 |
| API+ sucrose | 98.99 | 0.40 | 0.63 |
| API+ lactose | 98.86 | 0.42 | 0.67 |
| API+ glucose | 99.00 | 0.41 | 0.64 |

*API represents Pulsatilla saponin B4, the following API has the same meaning.

The data in Table 2 indicated that the purity of *Pulsatilla* saponin B4 in all composition comprising raw materials and excipients was equivalent on day 0, and there was no obvious difference in the content of related substances.

TABLE 3

Compatibility Test Results of Raw Materials and Excipients on day 7

| Raw Materials and Excipients | Content (%) | | | Related substances (%) | | | | | |
|---|---|---|---|---|---|---|---|---|---|
| | | | | 60° C. | | 40° C. | | illumination | |
| | 60° C. | 40° C. | illumination | Max single impurity | Total impurities | Max single impurity | Total impurities | Max single impurity | Total impurities |
| API | 98.93 | 98.96 | 98.97 | 0.41 | 0.66 | 0.40 | 0.64 | 0.40 | 0.64 |
| API + water for injection | 95.70 | 98.80 | 98.70 | 0.36 | 0.82 | 0.40 | 0.65 | 0.40 | 0.66 |
| API + physiological saline | 92.94 | 98.92 | 98.98 | 0.38 | 1.02 | 0.41 | 0.64 | 0.41 | 0.65 |
| API + mannitol | 98.89 | 98.99 | 98.91 | 0.40 | 0.65 | 0.39 | 0.60 | 0.41 | 0.66 |
| API + sucrose | 98.93 | 98.95 | 98.96 | 0.40 | 0.64 | 0.41 | 0.63 | 0.41 | 0.66 |
| API + lactose | 98.82 | 98.94 | 98.82 | 0.38 | 0.66 | 0.40 | 0.62 | 0.41 | 0.66 |
| API + glucose | 94.51 | 98.98 | 98.92 | 0.35 | 0.98 | 0.39 | 0.59 | 0.41 | 0.65 |

The data in Table 3 indicated that *Pulsatilla* saponin B4 itself and its composition with various excipients were much sensitive to temperature and illumination, its stability at high temperature (60° C.) was particularly affected by water for injection, physiological saline and glucose.

TABLE 4

Compatibility Test Results of Raw Materials and Excipients on day 14

| Raw Materials and Excipients | Content (%) | | | Related substances (%) | | | | | |
|---|---|---|---|---|---|---|---|---|---|
| | | | | 60° C. | | 40° C. | | illumination | |
| | 60° C. | 40° C. | illumination | Max single impurity | Total impurities | Max single impurity | Total impurities | Max single impurity | Total impurities |
| API | 98.89 | 98.86 | 98.95 | 0.41 | 0.64 | 0.41 | 0.63 | 0.42 | 0.64 |
| API + water for injection | 93.11 | 98.82 | 98.97 | 0.33 | 0.94 | 0.40 | 0.63 | 0.31 | 0.57 |

TABLE 4-continued

Compatibility Test Results of Raw Materials and Excipients on day 14

| Raw Materials and Excipients | Content (%) | | | Related substances (%) | | | | | |
|---|---|---|---|---|---|---|---|---|---|
| | | | | 60° C. | | 40° C. | | illumination | |
| | 60° C. | 40° C. | illumination | Max single impurity | Total impurities | Max single impurity | Total impurities | Max single impurity | Total impurities |
| API + physiological saline | 91.91 | 98.92 | 98.92 | 0.34 | 1.86 | 0.41 | 0.66 | 0.41 | 0.62 |
| API + mannitol | 98.91 | 98.91 | 98.93 | 0.38 | 0.62 | 0.40 | 0.63 | 0.40 | 0.62 |
| API + sucrose | 98.83 | 98.83 | 98.80 | 0.39 | 0.62 | 0.40 | 0.65 | 0.41 | 0.62 |
| API + lactose | 98.71 | 98.96 | 98.85 | 0.37 | 0.65 | 0.39 | 0.63 | 0.41 | 0.62 |
| API + glucose | 90.94 | 98.97 | 98.91 | 0.40 | 1.25 | 0.41 | 0.63 | 0.40 | 0.60 |

Compared with the results on day 7, the purity of *Pulsatilla* saponin B4 itself and its composition with mannitol, sucrose and lactose respectively did not further significantly decrease at 60° C., this indicated that the saponin had tended to be stable; however the purities of the saponin B4 in water for injection or physiological saline, and the composition with glucose further decreased, this indicated that the saponin was still degrading.

The compatibility test results of raw materials and excipients indicated that the compatibility of *Pulsatilla* saponin B4 with various excipients was fairly good under the conditions of 40° C. and illumination, the purity and the content of related substances had no obvious changes, and were relatively stable. However, the main active ingredients degrade to different degrees when the raw materials of *Pulsatilla* saponin B4 was mixed with water for injection, physiological saline or glucose at 60° C.; therefore, the aqueous injection or lyophilized powder of *Pulsatilla* saponin B4 for injection should avoid exposure to high temperature for long time during manufacture, storage and transportation.

1.2 Selection of Excipients

Commonly used lyophilized excipients include lactose, mannitol, sucrose, and glucose. *Pulsatilla* saponin B4, mannitol, lactose, glucose, and sucrose were weighed respectively according to the prescription shown in Table 5, and the intermediate solution was prepared by using the following process and lyophilized:

*Pulsatilla* saponin B4 was dissolved in an appropriate amount of water for injection, stirred to dissolve, added with the lyophilized excipients, stirred, the pH was adjusted to −7.0, 0.05 g of active carbon was added, the solution was heated and stirred at 100° C. for 15 min, cooled to room temperature, added with water for injection up to 100 g, filtered with a 0.22 μm microporous filter membrane to obtain the intermediate solution. 2 ml intermediate solution was weighed precisely and filled into a 10 ml vial, the temperature was reduced to −20° C. at a rate of 5.0° C./min in a freezing instrument, the vial was freezed at this temperature for 8 hours; then transferred to a freeze dryer, the temperature was raised to −10° C. at a constant rate of 25° C./3 h under a vacuum pressure of 5 Pa and kept for 8 h, the temperature was raised to 25° C. at a rate of 1.0° C./min under the same vacuum pressure and kept for 6 h.

The appearance of the lyophilized product prepared from various prescriptions was observed, and the purity of *Pulsatilla* saponin B4 and the content of related substances were investigated at the same time. The results were shown in Table 6.

TABLE 5

| | Prescriptions | | | |
|---|---|---|---|---|
| Compositions | F1 | F2 | F3 | F4 |
| API | 1.5 g | 1.5 g | 1.5 g | 1.5 g |
| mannitol | 5.0 g | — | — | — |
| sucrose | — | 5.0 g | — | — |
| lactose | — | — | 5.0 g | — |
| glucose | — | — | — | 5.0 g |
| water for injection | added to 100 g | added to 100 g | added to 100 g | added to 100 g |

TABLE 6

Selection Results of Excipients

| Items | | F1 | F2 | F3 | F4 |
|---|---|---|---|---|---|
| Intermediate solution | Appearance | Clear solution | Clear solution | Clear solution | Clear solution |
| | pH | 7.43 | 7.52 | 7.24 | 7.60 |
| | Content (%) | 99.14 | 99.15 | 99.16 | 99.14 |
| | Related substances (%) Max single impurity | 0.40 | 0.41 | 0.40 | 0.40 |
| | Total impurities | 0.64 | 0.65 | 0.65 | 0.64 |
| Lyophilized product | Appearance | White block | White block | White block | White, loose |
| | Water (%) | 0.14 | 0.15 | 0.14 | 0.18 |
| | Purity of API (%) | 99.02 | 98.34 | 98.07 | 94.03 |
| | Related substances (%) Max single impurity | 0.40 | 0.41 | 0.40 | 1.82 |
| | Total impurities | 0.64 | 1.23 | 1.25 | 4.53 |

From the results shown in Table 6, it can be seen that *Pulsatilla* saponin B4 degraded to different degrees after lyophilization when using lactose, sucrose or glucose as the excipient, the order of degradation was: glucose>sucrose>lactose; however when mannitol was used as the excipient, its content and related substances did not change significantly. Therefore, sucrose, lactose or mannitol was preferred as lyophilized excipients, and mannitol was most preferred.

1.3 Selection of Amount of Excipients

*Pulsatilla* saponin B4 and mannitol were weighed respectively according to the prescription shown in Table 7, the intermediate solution was prepared by using the following process and lyophilized:

*Pulsatilla* saponin B4 was dissolved in an appropriate amount of water for injection, stirred to dissolve, added with mannitol, stirred, the pH was adjusted to ~7.0, 0.05 g of active carbon was added, the solution was heated and stirred at 100° C. for 15 min, cooled to room temperature, added with water for injection up to 100 g, filtered with a 0.22 μm microporous filter membrane to obtain the intermediate solution. 2 ml intermediate solution was weighed precisely and filled into a 10 ml vial, the temperature was reduced to −20° C. at a rate of 5.0° C./min in a freezing instrument, the vial was freezed at this temperature for 8 hours; then transferred to a freeze drier, the temperature was raised to −10° C. at a constant rate of 25° C./3 h under a vacuum pressure of 5 Pa and kept for 8 h, the temperature was raised to 25° C. at a rate of 1.0° C./min under the same vacuum pressure and kept for 6 h.

The appearance of the lyophilized product prepared from various prescriptions was observed, and the purity of *Pulsatilla* saponin B4 and the content of related substances were investigated. The results were shown in Table 7.

preferably, the mass ratio of *Pulsatilla* saponin B4 to mannitol of the present invention is 3:10~3:16, most preferably 3:14.

1.4 Selection of pH in the Intermediate Solution

*Pulsatilla* saponin B4 is relatively sensitive to pH, and its degradation degree varies with the pH value. Therefore, the degradation of *Pulsatilla* saponin B4 at different pH was investigated, the optimal pH range was selected accordingly. The specific experimental steps were:

8 parts of *Pulsatilla* saponin B4 and mannitol were weighed respectively according to the prescription F8 in Table 7. *Pulsatilla* saponin B4 was dissolved in an appropriate amount of water for injection, stirred to dissolve, added with mannitol, stirred, the pH was adjusted according to table 8, 0.05 g of active carbon was added, the solution was heated and stirred at 100° C. for 15 min, cooled to room temperature, added with water for injection up to 100 g; filtered with a 0.22 μm microporous filter membrane to obtain the intermediate solution. 2 ml of the intermediate solution was filled into a 10 ml vial, the temperature was

TABLE 7

Prescriptions for Selection of Excipient Dosage and Results

| Prescriptions | | F5 | F6 | F7 | F8 | F9 | F10 |
|---|---|---|---|---|---|---|---|
| API:Mannitol | | 3:10 | 3:12 | 3:14 | 3:16 | 3:18 | 3:20 |
| API | | 1.5 g | 1.5 g | 1.5 g | 1.5 g | 1.5 g | 1.5 g |
| Mannitol | | 5 g | 6 g | 7 g | 8 g | 9 g | 10 g |
| Water for injection | | Add to 100 g | Add to 100 g | Add to 100 g | Add to 100 g | Add to 100 g | Add to 100 g |
| Intermediate solution | Appearance | Clear | Clear | Clear | Clear | Clear | Clear |
| | pH | 7.44 | 7.45 | 7.48 | 7.53 | 7.57 | 7.62 |
| | Content (%) | 99.11 | 99.09 | 99.10 | 99.10 | 99.09 | 99.09 |
| | Related substances (%) Max single impurity | 0.41 | 0.40 | 0.40 | 0.41 | 0.41 | 0.41 |
| | Total impurities | 0.64 | 0.64 | 0.65 | 0.64 | 0.65 | 0.64 |
| Lyophilized product | Appearance | White block | White block | White block | White block | White block | White block |
| | Water (%) | 0.15 | 0.13 | 0.14 | 0.15 | 0.14 | 0.14 |
| | Purity of API(%) | 98.84 | 98.93 | 99.08 | 98.86 | 97.85 | 97.68 |
| | Related substances (%) Max single impurity | 0.40 | 0.41 | 0.40 | 0.41 | 0.42 | 0.42 |
| | Total impurities | 0.94 | 0.97 | 0.64 | 0.89 | 1.03 | 1.04 |

From the results shown in Table 7, it can be seen that the amount of mannitol is not the more the better, it should be controlled in a suitable range. When the mass ratio of B4 to mannitol is between 3:10 and 3:14, the stability of B4 tends to increase as the amount of mannitol increases; thereafter, as the amount of mannitol further increases, the degradation of B4 in the lyophilized product is accelerated. Therefore, reduced to −20° C. at a rate of 5.0° C./min in a freezing equipment, the vial was freezed at the temperature for 8 hours; then transferred to a freeze dryer, the temperature was raised to −10° C. at a constant rate of 25° C./3 h under a vacuum pressure of 5 Pa and kept for 8 h, the temperature was raised to 25° C. at a rate of 1.0° C./min under the same vacuum pressure and kept for 6 h.

The results were shown in Table 8.

TABLE 8

Results under different pH conditions

| | | Nos. | | | | | | | |
|---|---|---|---|---|---|---|---|---|---|
| | | 1 | 2 | 3 | 4 | 5 | 6 | 7 | 8 |
| pH value of intermediate solution | | 5.5 | 6.0 | 6.5 | 7.0 | 7.5 | 8.0 | 8.5 | 9.0 |
| Appearance of lyophilized products | | White block | White block | White block | White block | White block | White block | White block | White block |
| Water (%) | | 0.22 | 0.18 | 0.19 | 0.17 | 0.16 | 0.17 | 0.22 | 0.78 |
| Related substances (%) | Max single impurity | 0.41 | 0.40 | 0.40 | 0.41 | 0.40 | 0.41 | 0.42 | 0.57 |
| | Total impurities | 0.92 | 0.77 | 0.65 | 0.66 | 0.64 | 0.64 | 0.79 | 1.21 |

From the results shown in Table 8, it can be seen that, taking the content of the related substances as an indicator, the pH value of the intermediate solution is preferably 6.0 to 8.5, and most preferably 6.5 to 8.0.

1.5 Selection of Amount of Active Carbon

The effect of the amount of active carbon and the adsorption time on the main ingredient were investigated, the specific steps were as below:

3 parts of *Pulsatilla* saponin B4 and mannitol were weighed respectively according to the prescription F8 in Table 7. *Pulsatilla* saponin B4 was dissolved in an appropriate amount of water for injection, stirred to dissolve, added with mannitol, stirred, added water for injection up to 100 ml, the pH was adjusted to ~7.0, the purity of *Pulsatilla* saponin B4 was determined; then the solution was added with active carbon according to Table 8, heated and stirred at 100° C. for 15 min, cooled to room temperature, part of the solution was filtered with a 0.22 µm microporous filter membrane and the pH value of the filtrate and the purity of *Pulsatilla* saponin B4 were detected; the remaining solution was stirred at 100° C. till the total adsorption lasted for 30 min, part of the solution was filtered with a 0.22 µm microporous filter membrane, and the pH value of the filtrate and the purity of *Pulsatilla* saponin B4 were detected.

The results were shown in Table 9.

intermediate solution, the amount (mass) of active carbon is preferably 0.05%~0.1%, more preferably 0.05%.

1.6 Study on Freeze Drying Process

The freeze drying process directly affects the appearance, re-dissolving rate, water and stability of the product. Therefore, the parameters of pre-freezing temperature, pre-freezing method, sublimation temperature, vacuum pressure, and desorption drying temperature were investigated, the specific steps were as below:

4 parts of *Pulsatilla* saponin B4 and mannitol were weighed respectively according to the prescription F8 in Table 7. *Pulsatilla* saponin B4 was dissolved in an appropriate amount of water for injection, stirred to dissolve, added with mannitol, stirred, the pH was adjusted to ~7, 0.05 g of active carbon was added, the solution was heated and stirred at 100° C. for 15 min, cooled to room temperature, added with water for injection up to 100 g; filtered with a 0.22 µm microporous filter membrane to obtain the intermediate solution. 2 ml of the intermediate solution was weighed precisely and filled into a 10 ml vial, the vial was freezed in a freezing equipment according to the parameters and conditions in Table 10; then transferred to a freeze-dryer, sublimation and desorption drying were performed according to the parameters and conditions in Table 10. The appearance of the lyophilized product was observed, the content of the related substances was determined, and the re-dissolving test was performed and the re-dissolution time was recorded. The results were shown in Table 10.

TABLE 9

Results of Effect of Amount of Active Carbon and Adsorption Duration on Main Ingredient

| Items | | Amount of Active Carbon (w/v) | | |
|---|---|---|---|---|
| | | 0.05% | 0.10% | 0.15% |
| Before adding carbon | Appearance | Clear solution | Clear solution | Clear solution |
| | pH | 7.43 | 7.55 | 7.71 |
| | Purity of API (%) | 99.11 | 99.13 | 99.12 |
| Absorbing for 15 min | Appearance | Clear solution | Clear solution | Clear solution |
| | pH | 7.45 | 7.51 | 7.69 |
| | Purity of API (%) | 99.02 | 98.92 | 98.73 |
| Absorbing for 30 min | Appearance | Clear solution | Clear solution | Clear solution |
| | pH | 7.41 | 7.53 | 7.63 |
| | Purity of API (%) | 98.88 | 98.21 | 98.05 |

The results of Table 9 show that the increase of the amount of active carbon and the prolongation of the adsorption duration will lead to the decrease of the purity of *Pulsatilla* saponin B4. Therefore, based on the volume of the

TABLE 10

Results of Effect of Different Freeze Drying Process Parameters on the Lyophilized Products

| | Groups | Process 1 | Process 2 | Process 3 | Process 4 |
|---|---|---|---|---|---|
| Parameters | pre-freezing temperature (° C.) | −15 | −20 | −25 | −30 |
| | Cooling mode | 1.0° C./min | 3.0° C./min | 5.0° C./min | 1.5° C./min |
| | sublimation temperature (° C.) | 0 | −10 | −10 | −10 |
| | rate during sublimation | 30° C./3 h | 25° C./3 h | 25° C./3 h | 30° C./3 h |
| | Vacuum pressure (Pa) | 0.5 | 5 | 0.1 | 10 |
| | Desorption drying temperature (° C.) | 30 | 25 | 25 | 30 |
| | Freeze drying cycle (h) | 26 | 32 | 32 | 24 |
| | Appearance | White block, without collapse | White block, without collapse | Foamy | White block, without collapse |
| | Water (%) | 0.21 | 0.14 | 0.72 | 0.33 |
| | Average re-dissolution time (second) | 6 | 5 | 6 | 8 |
| | Clarity of re-dissolving solution | Clear | Clear | Clear | Clear |
| Related substances(%) | Max single impurity | 0.89 | 0.40 | 1.13 | 0.56 |
| | Total impurities | 1.70 | 0.64 | 2.34 | 0.86 |

From the results shown in Table 10, it can be seen that the vacuum pressure during sublimation and desorption drying is a key parameter. If the vacuum pressure is too low (for example 0.1 Pa in Process 3), the lyophilized product obtained has a worse appearance and a high content of water, and the content of related substances is significantly higher than that in the products obtained by other processes, this indicates that *Pulsatilla* saponin B4 is more degraded. Therefore, the vacuum pressure is preferably 0.5 to 10 Pa, and more preferably 5 to 10 Pa.

Preferably, the steps of the freeze drying according to the present invention were as below:

the intermediate solution was sub-packed, the temperature was reduced to −30° C.~−15° C. at a rate of 3° C.~5° C./min or 1.0° C.~1.5° C./min, and the solution was freezed at the temperature for 8~10 hours; then put in a closed equipment, the temperature was raised to −10° C.~0° C. at a constant rate of 25° C.~30° C./3 h under a vacuum pressure of 0.5~10 Pa and kept for 8~10 h, the temperature was raised to 25° C.~30° C. at a rate of 1.0° C.~1.5° C./min under the same vacuum pressure and kept for 4~6 hours.

Preferably, the steps of freeze drying according to the present invention were as below:

the intermediate solution was sub-packed, the temperature was reduced to −30° C.~−20° C. at a rate of 3.0° C.~5.0° C./min or 1.0° C.~1.5° C./min in a freeze equipment, and the solution was freezed at the temperature for 8~10 hours; then put in a closed equipment, the temperature was raised to −10° C. at a constant rate of 25° C.~30° C./3 h under a vacuum pressure of 5~10 Pa and kept for 8 h, the temperature was raised to 25° C.~30° C. at a rate of 1.0° C.~1.5° C./min under the same vacuum pressure and kept for 4 h.

Based on the results of the present Experimental Example, the lyophilized powder of *Pulsatilla* saponin B4 for injection according to the present invention comprises *Pulsatilla* saponin B4 and a lyophilized excipient, wherein the lyophilized excipient is one or more in any ratio selected from the group consisting of mannitol, sucrose and lactose, preferably mannitol; and the mass ratio of *Pulsatilla* saponin B4 to the lyophilized excipient is 3:10~3:16, more preferably 3:14.

Preferably, the lyophilized powder of *Pulsatilla* saponin B4 for injection comprises *Pulsatilla* saponin B4 and a lyophilized excipient in a mass ratio of 3:10~3:16; and further comprises small amount of unavoidable impurities such as water and degradation products of *Pulsatilla* saponin B4.

The preparation method of the lyophilized powder of *Pulsatilla* saponin B4 for injection according to the present invention is:

I. Preparation of the Intermediate Solution

*Pulsatilla* saponin B4 was dissolved in an appropriate amount of water for injection, stirred to dissolve, added with the lyophilized excipient according to the weight ratio, stirred, the pH was adjusted to 6.0~8.5, the solution was added with 0.05%~0.1% of active carbon based on the total mass of the intermediate solution, heated and stirred at 100° C. for 10~20 min, cooled to room temperature, added with water for injection till the concentration of *Pulsatilla* Saponin B4 was 0.5%~5%, and filtered with a 0.22 Lm microporous filter membrane to obtain the intermediate solution;

II. Freeze Drying the intermediate solution prepared in the Step I was sub-packed; transferred to a freezing equipment, the temperature was reduced to −30° C.~−15° C. at a rate of 3.0° C.~5.0° C./min or 1.0° C.~1.5° C./min, and the solution was freezed at the temperature for 8~10 hours; then put in a closed equipment, the temperature was raised to −10° C.~0° C. at a constant rate of 25° C.~30° C./3 h under a vacuum pressure of 0.5~10 Pa and kept for 8~10 h, the temperature was raised to 25° C.~30° C. at a rate of 1.0° C.~1.5° C./min under the same vacuum pressure and kept for 4~6 hours.

Preferably, the preparation method is as follows:

I. Preparation of the Intermediate Solution

*Pulsatilla* saponin B4 was dissolved in water for injection, stirred to dissolve, added with the lyophilized excipients according to the weight ratio, stirred, the pH was adjusted to 6.5~8.0, the solution was added with 0.05% of active carbon based on the total mass of the intermediate solution, heated and stirred at 100° C. for 10~20 min, cooled to room temperature, added injection water till the concentration of *Pulsatilla* saponin B4 was 2%~3%, and filtered with a 0.22 μm microporous filter membrane to obtain the intermediate solution;

II. Freeze Drying the intermediate solution prepared in Step I was sub-packed; transferred to a freezing equipment, the temperature was reduced to −30° C.~−20° C. at a rate of 3.0° C.~5.0° C./min or 1.0° C.~1.5° C./min, and the solution was freezed at the temperature for 8 hours; then put in a closed equipment, the temperature was raised to −10° C. at a constant rate of 25° C.~30° C./3 h under a vacuum pressure of 5~10 Pa and kept for 8 h, the temperature was raised to 25° C. at a rate of 1.0° C.~1.5° C./min under the same vacuum pressure and kept for 4 h.

Example 2 A Lyophilized Powder of *Pulsatilla* Saponin B4 for Injection

Prescription of an intermediate solution:

| | |
|---|---|
| *Pulsatilla* saponin B4 raw material | 2.5 g |
| Mannitol | 5.0 g |
| Water for injection | Added to 100 ml |
| Prepared into | 100 ml |

The lyophilized powder for injection was prepared by the method as below:

I. Preparation of the Intermediate Solution

A prescribed amount of *Pulsatilla* Saponin B4 was taken and weighed precisely, an appropriate amount of water for injection was added, the *Pulsatilla* Saponin B4 raw material was completely dissolved under magnetic stirring, a prescribed amount of mannitol was added into this solution, stirred to dissolve completely and stirring was continued for about 10 minutes, 0.05 g active carbon was added, then the system was heated and stirred in 100° C. water bath for 15 min, cooled to room temperature, water for injection was added to 100 ml, shaken well, filtered with a 0.22 μm microporous filter membrane to remove the active carbon, then the intermediate solution was obtained;

II. Freeze Drying

The intermediate solution prepared in the Step I was sub-packed: 2 ml intermediate solution was weighed precisely and filled into a 10 ml vial; the vial was transferred to a freezing instrument, cooled down to −20° C. at full speed and the temperature was kept for 8 h; then the vial was transferred to a freeze dryer, the temperature was raised to −10° C. at a constant rate of 25° C./3 h under a vacuum pressure of 5 Pa, the temperature was kept at −10° C. for 8 h, the temperature was raised to 25° C. at a constant speed, kept for 4 h, the lyophilized powder for injection was obtained accordingly.

The prepared lyophilized powder of *Pulsatilla* saponin B4 for injection was a white fluffy block, the reconstitution time in water was 6 s, the water content was 1.3%, the purity of *Pulsatilla* saponin B4 was 99.74%, the content of maximum single impurity was 0.12%, and the content of total impurity was 0.26%.

Example 3 A Lyophilized Powder of *Pulsatilla* Saponin B4 for Injection

Prescription of an intermediate solution:

| | |
|---|---|
| *Pulsatilla* saponin B4 | 2.5 g |
| Lactose | 5.0 g |
| Water for injection | Added to 100 ml |
| Prepared into | 100 ml |

The lyophilized powder for injection was prepared by the method as below:

I. Preparation of the Intermediate Solution

A prescribed amount of *Pulsatilla* saponin B4 was taken and weighed precisely, an appropriate amount of water for injection was added, the *Pulsatilla* saponin B4 raw material was completely dissolved under magnetic stirring, a prescribed amount of lactose was added into this solution, stirred to dissolve completely and stirring was continued for about 10 minutes, 0.1 g active carbon was added, then the system was heated and stirred in 100° C. water bath for 20 min, cooled to room temperature, water for injection was added to 100 ml, shaken well, filtered with a 0.22 μm microporous filter membrane to remove the active carbon, then the intermediate solution was obtained;

II. Freeze Drying

The intermediate solution prepared in the Step I was sub-packed: 2 ml intermediate solution was weighed precisely and filled into a 10 ml vial; the vial was transferred to a freezing instrument, cooled down to −30° C. at a rate of 3° C./min and the temperature was kept for 10 h; then the vial was transferred to a freeze dryer, the temperature was raised to −10° C. at a constant rate of 25° C./3 h under a vacuum pressure of 10 Pa, the temperature was kept at −10° C. for 10 h, the temperature was raised to 30° C. at a rate of 1.5° C./min, the temperature was kept for 6 h, the lyophilized powder for injection was obtained accordingly.

The prepared lyophilized powder of *Pulsatilla* saponin B4 for injection was a white fluffy block, the reconstitution time in water was 6 s, the water content was 1.07%, the purity of *Pulsatilla* saponin B4 was 99.51%, the content of maximum single impurity was 0.28%, and the content of total impurity was 0.39%.

Example 4 A Lyophilized Powder of *Pulsatilla* Saponin B4 for Injection

Prescription of an intermediate solution:

| | |
|---|---|
| *Pulsatilla* Saponin B4 | 2.5 g |
| sucrose | 5.0 g |
| Water for injection | Added to 100 ml |
| Prepared into | 100 ml |

The lyophilized powder for injection was prepared by the method as below:

I. Preparation of the Intermediate Solution

A prescribed amount of *Pulsatilla* Saponin B4 was taken and weighed precisely, an appropriate amount of water for injection was added, the *Pulsatilla* saponin B4 raw material was completely dissolved under magnetic stirring, a prescribed amount of sucrose was added into this solution, stirred to dissolve completely and stirring was continued for about 10 minutes, 0.15 g active carbon was added, then the system was heated and stirred in 100° C. water bath for 15 min, cooled to room temperature, water for injection was added to 100 ml, shaken well, filtered with a 0.22 μm microporous filter membrane to remove the active carbon, then the intermediate solution was obtained;

II. Freeze Drying

The intermediate solution prepared in the Step I was sub-packed: 2 ml intermediate solution was weighed precisely and filled into a 10 ml vial; the vial was transferred to a freezing instrument, cooled down to −15° C. at a rate of 5° C./min and the temperature was kept for 9 h; then the vail was transferred to a freeze dryer, the temperature was raised to 0° C. at a constant rate of 30° C./3 h under a vacuum pressure of 0.5 Pa, the temperature was kept at 0° C. for 8 h, the temperature was raised to 25° C. at a rate of 1° C./min, kept for 5 h, the lyophilized powder for injection was obtained accordingly.

The prepared lyophilized powder of *Pulsatilla* saponin B4 for injection is a white fluffy block, the reconstitution time in water was 6 s, the water content was 1.39%, the purity of *Pulsatilla* saponin B4 was 99.68%, the content of maximum single impurity was 0.22%, and the content of total impurity was 0.32%.

In summary, the present invention provides a preparation of *Pulsatilla* saponin B4 for injection, including aqueous injection and lyophilized powder for injection. Compared with oral preparation, the injection preparation provided by the present invention significantly reduces the effective dose of *Pulsatilla* saponin B4 in reversing cisplatin-induced renal injury, which improves the safety of medication. In addition, the indicators of the preparation for injection of the present invention are stable and controllable through optimizing the parameters of the preparation process.

The invention claimed is:

1. A *Pulsatilla* saponin B4 preparation for injection, consisting of *Pulsatilla* saponin B4, a pharmaceutically acceptable excipient and 1.91% or less in amount of unavoidable impurities based on a total weight of the *Pulsatilla* saponin B4 preparation for injection, wherein the preparation is a lyophilized powder for injection, and pharmaceutically acceptable excipient is a lyophilized excipient, which is one or more in any ratio selected from the group consisting of lactose, sucrose and mannitol, wherein the mass ratio of the *Pulsatilla* saponin B4 to the lyophilized excipient in the lyophilized powder for injection is 3:10~3:16;

the lyophilized powder for injection is prepared by the method comprising the following steps:

preparation of the intermediate solution: dissolving the *Pulsatilla* saponin B4 into water for injection, stirring to dissolve, adding the lyophilized excipient according to the mass ratio, stirring, adjusting the pH to 6.0~8.5, adding 0.05%~0.1% of the active carbon based on the total mass of the intermediate solution, heating at 100° C. and stirring for 10~20 min, cooling to room temperature, adding water for injection till the concentration of the *Pulsatilla* saponin B4 is 0.5%~5%, filtering with a 0.22 μm microporous filter membrane to obtain the intermediate solution;

freeze-drying operation: sub-packing the intermediate solution, transferring into a freezing equipment, reducing the temperature to −30° C.−−15° C. at a rate of 3.0° C.~5.0° C./min or 1.0° C.~1.5° C./min, and freezing at this temperature for 8~10 hours; then placing in a closed equipment, raising evenly the temperature to −10° C.~0° C. at a rate of 25° C.~30° C./3 h under a vacuum pressure of 0.5~10 Pa, keeping at this temperature for 8~10 h, raising the temperature to 25° C.~30° C. at a rate of 1.0° C.~1.5° C./min under the same vacuum pressure, and keeping at this temperature for 4~6 hours.

2. The *Pulsatilla* saponin B4 preparation for injection according to claim 1, wherein, the *Pulsatilla* saponin B4 preparation for injection is an intravenous injection and/or an intramuscular injection.

3. The *Pulsatilla* saponin B4 preparation for injection according to claim 1, wherein,
the mass ratio of *Pulsatilla* saponin B4 to the lyophilized excipient in the lyophilized powder for injection is 3:14.

4. The *Pulsatilla* saponin B4 preparation for injection according to claim 1, wherein, the lyophilized excipient is mannitol.

5. The *Pulsatilla* saponin B4 preparation for injection according to claim 1, wherein the preparation of the intermediate solution is as follows:
dissolving the *Pulsatilla* saponin B4 into water for injection, stirring to dissolve, adding the lyophilized excipient according to the mass ratio, stirring, adjusting the pH to 6.5~8.0, adding 0.05% of active carbon based on the total mass of the intermediate solution, heating at 100° C. and stirring for 10~20 min, cooling to room temperature, adding water for injection till the concentration of the *Pulsatilla* saponin B4 is 2%~3%, and filtering with the 0.22 μm microporous filter membrane to obtain the intermediate solution.

6. The *Pulsatilla* saponin B4 preparation for injection according to claim 1, wherein the freeze-drying operation is as follows:
sub-packing the intermediate solution, transferring into the freezing equipment, reducing the temperature to −30° C.~−20° C. at the rate of 3.0° C.~5.0° C./min or 1.0° C.~1.5° C./min, and freezing at this temperature for 8 hours; then placing in the closed container, raising the temperature evenly to −10° C. at the rate of 25° C.~30° C./3 h under a vacuum pressure of 5~10 Pa, keeping at this temperature for 8 hours, raising the temperature to 25° C. at the rate of 1.0° C.~1.5° C./min under the same vacuum pressure, and keeping at this temperature for 4 hours.

7. A method for preparing a lyophilized powder of *Pulsatilla* saponin B4 for injection,
wherein, the lyophilized powder of *Pulsatilla* saponin B4 for injection is the *Pulsatilla* saponin B4 preparation defined as claim 1 comprising the steps of the preparation and freeze-drying of the intermediate solution;
wherein, the preparation of the intermediate solution is as follows:
dissolving the *Pulsatilla* saponin B4 into water for injection, stirring to dissolve, adding the lyophilized excipient according to the mass ratio, stirring, adjusting the pH to 6.0~8.5, adding 0.05%~0.1% of the active carbon based on the total mass of the intermediate solution, heating at 100° C. and stirring for 10~20 min, cooling to room temperature, adding water for injection till the concentration of the *Pulsatilla* saponin B4 is 0.5%~5%, filtering with the 0.22 μm microporous filter membrane to obtain the intermediate solution;
wherein the freeze-drying operation is as follows:
sub-packing the intermediate solution, transferring into the freezing equipment, reducing the temperature to −30° C.~−15° C. at the rate of 3.0° C.~5.0° C./min or 1.0° C.~1.5° C./min, and freezing at this temperature for 8~10 hours; then placing in the closed equipment, raising evenly the temperature to −10° C.~0° C. at the rate of 25° C.~30° C./3 h under the vacuum pressure of 0.5~10 Pa, keeping at this temperature for 8~10 h, raising the temperature to 25° C.~30° C. at the rate of 1.0° C.~1.5° C./min under the same vacuum pressure, and keeping at this temperature for 4~6 hours.

8. The method according to claim 7, wherein
the freeze-drying operation is as follows:
sub-packing the intermediate solution, transferring into the freezing equipment, reducing the temperature to −30° C.~−20° C. at the rate of 3.0° C.~5.0° C./min or 1.0° C.~1.5° C./min, and freeze at this temperature for 8 hours; then placing in the closed container, raising evenly the temperature to −10° C. at the rate of 25° C.~30° C./3 h under the vacuum pressure of 5~10 Pa, keeping at this temperature for 8 h, raising the temperature to 25° C. at the rate of 1.0° C.~1.5° C./min under the same vacuum pressure, and keeping at this temperature for 4 h.

9. The method according to claim 7, wherein the preparation of the intermediate solution is as follows: dissolving the *Pulsatilla* saponin B4 into water for injection, stirring to dissolve, adding the lyophilized excipient according to the mass ratio, stirring, adjusting the pH to 6.5~8.0, adding 0.05% of active carbon based on the total mass of the intermediate solution, heating at 100° C. and stirring for 10 20 min, cooling to room temperature, adding water for injection until the concentration of the *Pulsatilla* saponin B4 is 2%~3%, filtering with the 0.22 μm microporous filter membrane to obtain the intermediate solution.

* * * * *